(12) United States Patent
Ohi et al.

(10) Patent No.: US 6,981,401 B2
(45) Date of Patent: *Jan. 3, 2006

(54) METHOD FOR TESTING PROPERTIES OF CORROSIVE LUBRICANTS

(75) Inventors: James Ohi, Denver, CO (US); Jose L. De La Cruz, San Antonio, TX (US); Paul I. Lacey, Wexford (IE)

(73) Assignee: Southwest Research Institute, San Antonio, TX (US)

(*) Notice: Subject to any disclaimer, the term of this patent is extended or adjusted under 35 U.S.C. 154(b) by 86 days.

This patent is subject to a terminal disclaimer.

(21) Appl. No.: 10/721,305

(22) Filed: Nov. 25, 2003

(65) Prior Publication Data

US 2005/0109130 A1   May 26, 2005

(51) Int. Cl.
*G01N 19/02* (2006.01)
(52) U.S. Cl. .................... 73/10; 73/865.6; 73/9
(58) Field of Classification Search ............... 73/865.6, 73/10, 9
See application file for complete search history.

(56) References Cited

U.S. PATENT DOCUMENTS

| | | | |
|---|---|---|---|
| 3,166,927 A | 1/1965 | Sonntag | |
| 3,302,447 A | 2/1967 | Mertwoy | |
| 3,785,196 A | 1/1974 | Smith | |
| 3,913,337 A | 10/1975 | Merjan | |
| 4,009,606 A | 3/1977 | Clebant et al. | |
| 4,228,674 A | 10/1980 | Mertwoy | |
| 4,253,326 A | 3/1981 | Muennich | |
| 4,311,036 A | 1/1982 | Kajdas et al. | |
| 4,491,373 A | 1/1985 | Sugi et al. | |
| 4,939,922 A | 7/1990 | Smalley | |
| 5,022,229 A | 6/1991 | Vitale | |
| 5,281,535 A | 1/1994 | Wei et al. | |
| 5,515,712 A | 5/1996 | Yunick | |
| 5,865,070 A | 2/1999 | Bornhorst et al. | |
| 6,070,456 A | 6/2000 | Cameron et al. | |
| 6,109,617 A | 8/2000 | Laney | |
| 6,546,782 B1 * | 4/2003 | De La Cruz et al. ............ 73/7 |

OTHER PUBLICATIONS

Lacey, et al., Effects of High Temperature and Pressure on Fuel Lubricated Wear, Society of Automotive Engineers, Inc., 2001.

* cited by examiner

*Primary Examiner*—Hezron Williams
*Assistant Examiner*—Rodney Frank
(74) *Attorney, Agent, or Firm*—Paula D. Morris; The Morris Law Firm, P.C.

(57) ABSTRACT

A method of testing corrosive lubricating media using a wear testing apparatus without a mechanical seal. The wear testing apparatus and methods are effective for testing volatile corrosive lubricating media under pressure and at high temperatures.

86 Claims, 5 Drawing Sheets

METHOD FOR TESTING PROPERTIES OF CORROSIVE LUBRICANTS

STATEMENT REGARDING FEDERALLY SPONSORED RESEARCH

The United States Government has a paid-up license in this application and the right in limited circumstances to require the patent owner to license others on reasonable terms as provided for by the terms of Contract No. YXE-8-18033-01 awarded by the National Renewable Energy Laboratory.

CROSS-REFERENCE TO RELATED APPLICATIONS

This application is related to U.S. Pat. No. 6,546,782 B1.

FIELD

This application relates to an apparatus and method for testing lubricating properties of fluids and wear resistance of materials.

BACKGROUND

Fuel system components employed in some modern ground and aviation equipment rely on the fuel passing through them for lubrication of sliding contacts. Some of these components experience extreme temperature and pressure conditions in operating engines. One such component is the fuel injector used in diesel engines.

One way to examine the efficacy of fuel compositions as lubricants and the resistance of materials to the wear mechanisms experienced in fuel injectors would be to construct full-scale working units and run them in test engines, examining them afterwards for wear. This approach is both costly and time consuming. It is of great utility in the transportation industry to predict the efficacy of fuel compositions in providing lubrication and the wear resistance of various materials of construction without having to construct and operate full scale equipment under conditions duplicating the operating conditions to which the equipment would be subject when in use.

Typical equipment used for testing lubricity uses a mechanism to impart motion between two samples of material with the lubricant of interest interposed between the samples. The lubricating ability of the lubricant under study is determined either by studying the rate of wear of standard sample materials with different lubricants under the same conditions of load and motion, or to measure the amount of torque transmitted between a driving mechanism holding one sample and a driven mechanism holding the other sample when a given lubricant is interposed between the driving and driven samples. Both schemes have been employed in bench top scale equipment and attempts have been made to correlate the results thus obtained with the results obtained from employing full-scale equipment in an operating engine.

Such testing equipment include a sealed chamber that affords reciprocating contact between test surfaces while maintaining the lubricant inside the sealed chamber. Mechanical seals, such as O-rings or other gasket materials, have proven ineffective when testing corrosive lubricating media samples. Corrosive lubricants break down mechanical seals allowing the seals to become an additive of the lubricant. A need exists for an apparatus that allows for testing corrosive lubricating media while also maintaining a sealed chamber under pressure and at elevated temperatures during operation.

SUMMARY

A method of safely testing at least one lubrication property of a flammable corrosive volatile lubricating media under operating engine conditions. The method comprising providing a testing chamber comprising a workpiece; sealing the testing chamber using one or more features of an actuator rod selected from the group consisting of a deviation from linearity through a longitudinal retaining bore and a clearance through the longitudinal retaining bore, the one or more features being effective to maintain the lubricating media at a pressure gradient sufficient to simulate said engine conditions between the testing chamber and the outside of the testing chamber while permitting the actuator rod to move freely through the longitudinal retaining bore. The method further comprising equalizing pressure within the testing chamber to maintain said pressure at a maximum safe pressure; subjecting the workpiece to operating engine conditions comprising a selected pressure and a selected temperature; imparting to the workpiece a contact force having a magnitude and for a number of cycles effective to simulate said operating engine conditions; and, providing a vent effective to prevent the pressure from exceeding the maximum safe pressure in the testing chamber.

DETAILED DESCRIPTION

Wear Testing Apparatus

The present application provides a wear testing apparatus and methods effective for testing corrosive lubricating media without the need for a mechanical seal. The wear testing apparatus and methods are effective for testing volatile corrosive lubricating media under pressure and at elevated temperatures. A preferred wear testing apparatus for use in the method is described in U.S. Pat. No. 6,546,782 B1, incorporated herein by reference. Briefly, the '782 apparatus comprises: (1) a testing chamber containing a workpiece holding and contacting assembly, mechanical pop-off valve, and a blow-out panel, (2) an actuator rod, (3) an actuator rod support arm, (4) a longitudinal retaining bore, (5) a motion generator, (6) a seal between the actuator rod and the testing chamber, (7) at least one sealable conduit communicating with the testing chamber for gas flow, and (8) a cranking assembly.

Corrosive Lubricating Media

During testing conditions, the testing chamber of the present apparatus preferably contains volatile corrosive lubricating media in the form of condensed fluid. The corrosive lubricating media may be any corrosive liquid capable of use in wear testing, such as described in ASTM testing standard D6079. Preferably, corrosive lubricating media comprise fuel compositions used in or of potential utility in compression ignition and glow ignition diesel engines. Preferred corrosive lubricating media include, but are not necessarily limited to, ethers and alcohols. More preferred corrosive lubricating media are selected from, but not necessarily limited to, dimethyl ether (DME), methyl tertiary-butyl ether (MTBE), ethyl tertiary butyl ether (ETBE), ethanol, and methanol. Most preferred corrosive lubricating media are selected from, but not necessarily limited to, dimethyl ether (DME). Corrosive lubricating media, such as DME, attacks and degrades seals made primarily of materials, including but not necessarily limited to, rubber, teflon and polytetrafluoroethylene (PTFE). Once degraded, the constituents of a given seal become part of the lubricating media causing cross contamination, and giving false data during testing. The degradation of a seal under operating pressures also allows volatile lubricating media to escape the testing chamber, which is likely to cause a flash reaction or explosion.

The volume of corrosive lubricating media used in the testing chamber must be adjusted so that it does not introduce buoyancy effects into the test. The method of using the apparatus is described in ASTM testing standard D6079 as an example. Though the present apparatus is well suited to carry out the essential features of this testing standard, other testing protocols are equally well carried out using the same general equipment and procedures.

Operation of Wear Testing Apparatus

In preparation for a test, testing chamber 101 (FIG. 1) is pressurized via valve 176 to a predetermined value. It is not necessary to use high-pressure gas; however, if high-pressure gas is used, high-pressure gas flow is applied substantially simultaneously to support arm 110 via valve 182 and conduit 170. Preferred gases include, but are not necessarily limited to, inert gases. Inert gases include, but are not necessarily limited to nitrogen, helium, and argon. A most preferred gas is nitrogen.

Figure 1:
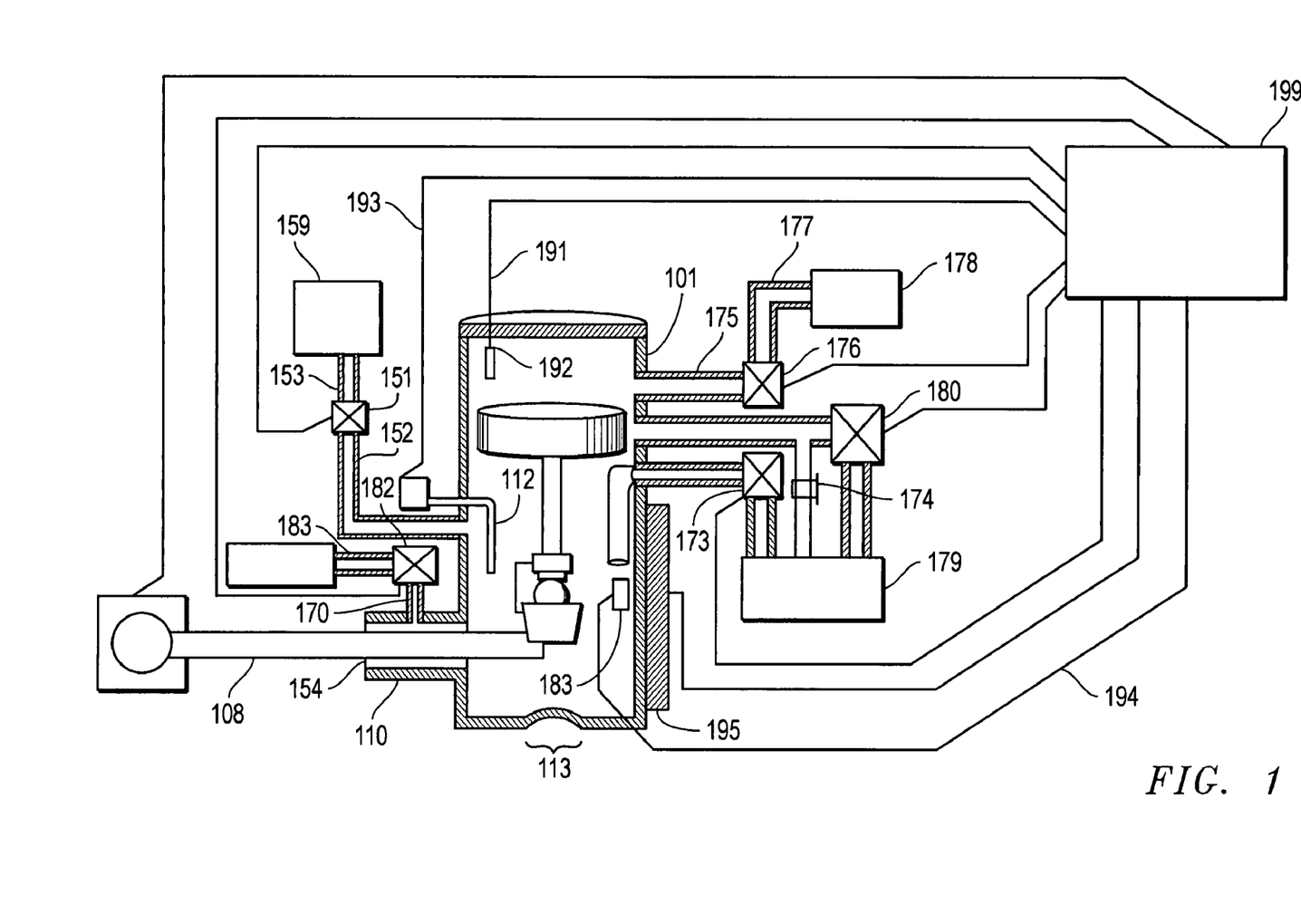
FIG. 1 is a schematic block diagram of the arrangement and connectivity of the elements of the testing apparatus and the control and sensor lines utilized by the automatic control device.

When actuator rod 108 is within the bore of actuator rod support arm 110, the testing chamber 101 is sealed from the ambient environment by the combination of the small clearance between actuator rod 108 and the bore of actuator rod support arm 110 together with the low deviation from linearity of the actuator rod 108 and the bore through actuator rod support arm 110. If desired, gas pressure may be supplied via valve 182 to the annular space 154. With further reference to FIG. 1, actuator rod 108 is supported by actuator rod support arm 110, which is rigidly fixed to testing chamber 101. Actuator rod support arm 110 maintains gas within testing chamber 101 at pressures of at least 70 psi, and constrains actuator rod 108 to movement normal to the major axis of testing chamber 101 when the actuator rod is actuated.

If the corrosive lubricating media is a gas under ambient conditions, one such example being DME, the testing chamber is purged with inert gas 178, as detailed in U.S. Pat. No. 6,546,782 B1, preferably using repeated pressure/vent cycles, then vented 179 to near ambient pressure. A quantity of the gaseous media to be tested 159 is then charged into testing chamber 101 via conduit 152. Flow through conduit 152 is controlled by valve 151. A source of the gaseous corrosive lubricating media is connected to the inlet side of valve 151 via conduit 153. Additional sources of gaseous reagents as well as inert gas for purging the apparatus may be connected to conduit 153 through tee and valve arrangements such as are well known to one practiced in the art. Alternative embodiments of the present application may also include a separate valve and conduit affixed directly to testing chamber 101 for each gas contemplated to be introduced to testing chamber 101. Once a sufficient quantity of the gaseous corrosive lubricating media has been condensed into testing chamber 101, the testing chamber is pressurized with inert gas to a predetermined pressure. The pressure is determined by the environmental conditions that will be simulated during the test. Where the corrosive lubricating media is not flammable when heated, purging the apparatus with inert gas 178 prior to charging it with corrosive lubricating media is not required. In such testing conditions, conduits 175 and 177 and valve 176 may be eliminated from the testing apparatus.

Where the corrosive lubricating media has a high vapor pressure, the apparatus is charged with an amount of corrosive lubricating media condensate that considerably submerges the contact point of the workpieces in the sealed chamber. This is done to insure that the contact point will still be submerged after the testing chamber is heated to the test temperature. When the condensed corrosive lubricating media is heated, a portion of the condensate will vaporize until enough of the corrosive lubricating media has vaporized that the vapor phase material is in equilibrium with the condensate. Submerging the contact point prior to heating insures that it will still be immersed when enough of the lubricant media condensate has vaporized to establish an equilibrium vapor pressure within the testing chamber. This is to say that during heating, the pool of condensate will not have vaporized to a point that leaves the contact point between workpieces in the vapor, rather than in the condensate, following heating of the testing apparatus and condensate sample.

Once the testing chamber has been charged with testing materials, the chamber is heated to a predetermined value using heater 195 and the feedback loop comprising sensor 112 and sensor line 193 if the apparatus is so equipped. Where the apparatus is computer controlled during heating and the conduct of the experiment, the gas pressure within testing chamber 101 is controlled by pressure sensor 192, control line 191, and vent valve 180 in a closed loop feed back arrangement. Fluid level covering the workpieces is also controlled by a feed back loop comprised of level sensor 183, sensor line 194, and fluid vent valve 173. If testing chamber 101 is not equipped with the various sensors and control hardware and software 199, described in U.S. Pat. No. 6,546,782 B1, incorporated herein by reference, pressure and level are adjusted manually during the course of the experiment by the apparatus operator.

With further reference to FIG. 1, other features incorporated into testing chamber 101 are venting mechanisms. In a preferred embodiment, the venting mechanisms are blow-out panel 113 and mechanical pop-off valve 174. The blow-out panel 113 and mechanical pop-off valve 174 allow for safe operation and avoid explosion during testing of volatile fluids under pressure and at elevated temperatures. In situations concerning high-pressure failure, the testing chamber 101 is capable of venting off through either mechanical pop-off valve 174 or blow-out panel 113, or both. Blow-out panel 113 is designed to fail, relieving pressure in a controlled manner, in the event that a pressure excursion that could not be equalized by venting testing chamber 101 through valve 180 should occur within the testing chamber. An example of such an event would be the pressure wave associated with an explosion occurring in testing chamber 101 during a test. In a preferred embodiment, blow-out panel 113 is designed to fail at a pressure of about 3400 psi. Pressure maximums may vary depending on the parameters of a given test.

Figure 2:
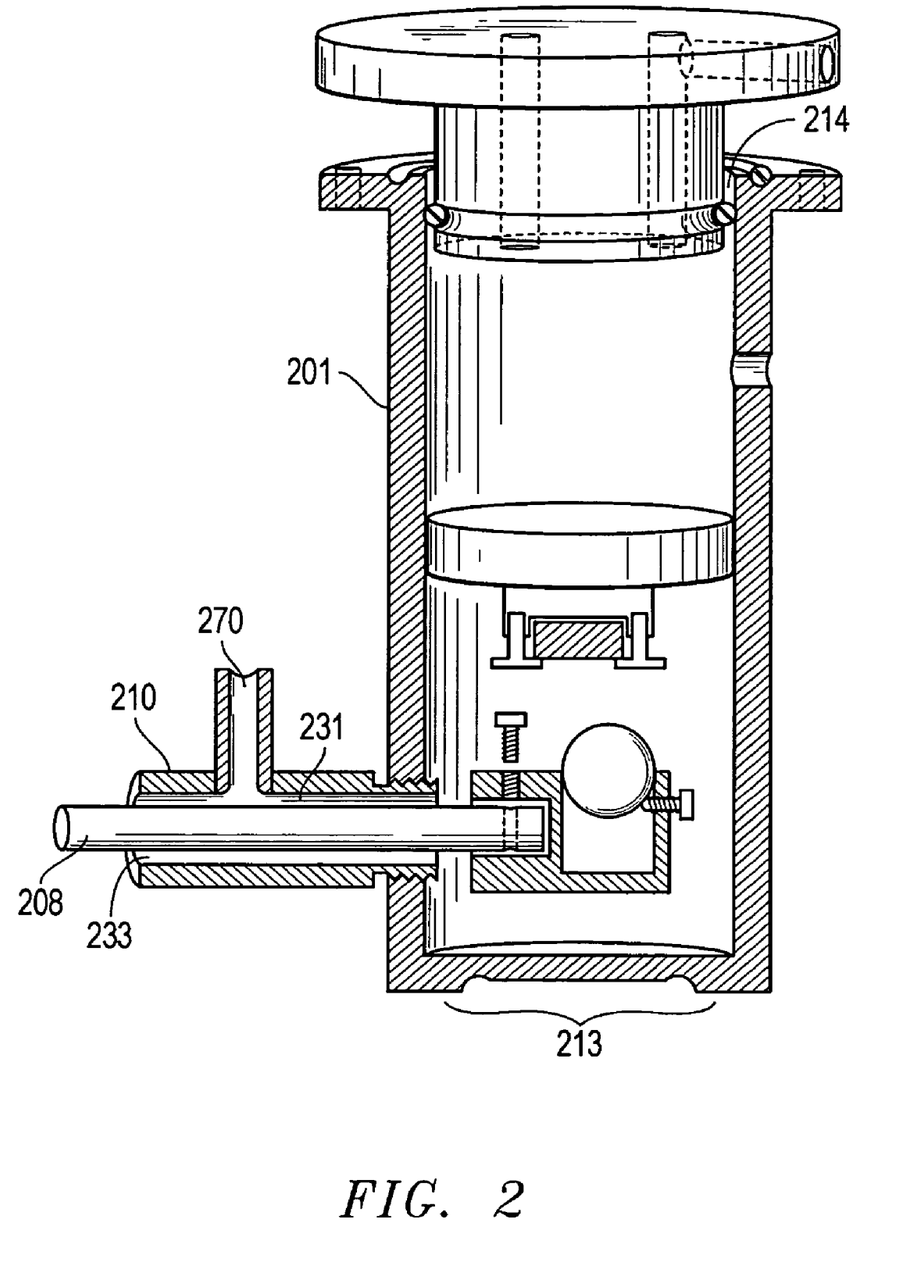
FIG. 2 is a cutaway elevation view of the testing chamber, cap, and actuator rod support arm with the actuator rod, workpiece loading device and workpiece chucks installed.

Further details of the mechanical features of testing chamber 101 are disclosed in FIG. 2, which is described in detail in U.S. Pat. No. 6,546,782 B1. FIG. 2 is a cutaway elevation view of the testing chamber and the components it contains when assembled for a test. With reference to FIG. 2, testing chamber 201, which is equivalent to testing chamber 101 of FIG. 1 is oriented with the long axis of the cylinder approximately vertical, with blow out panel 213 facing down and testing chamber opening 214 facing up. In this orientation, actuator rod support arm 210, which is equivalent to actuator rod support arm 110 of FIG. 1 and its equivalents disclosed below, is oriented more or less horizontally.

Figure 3:
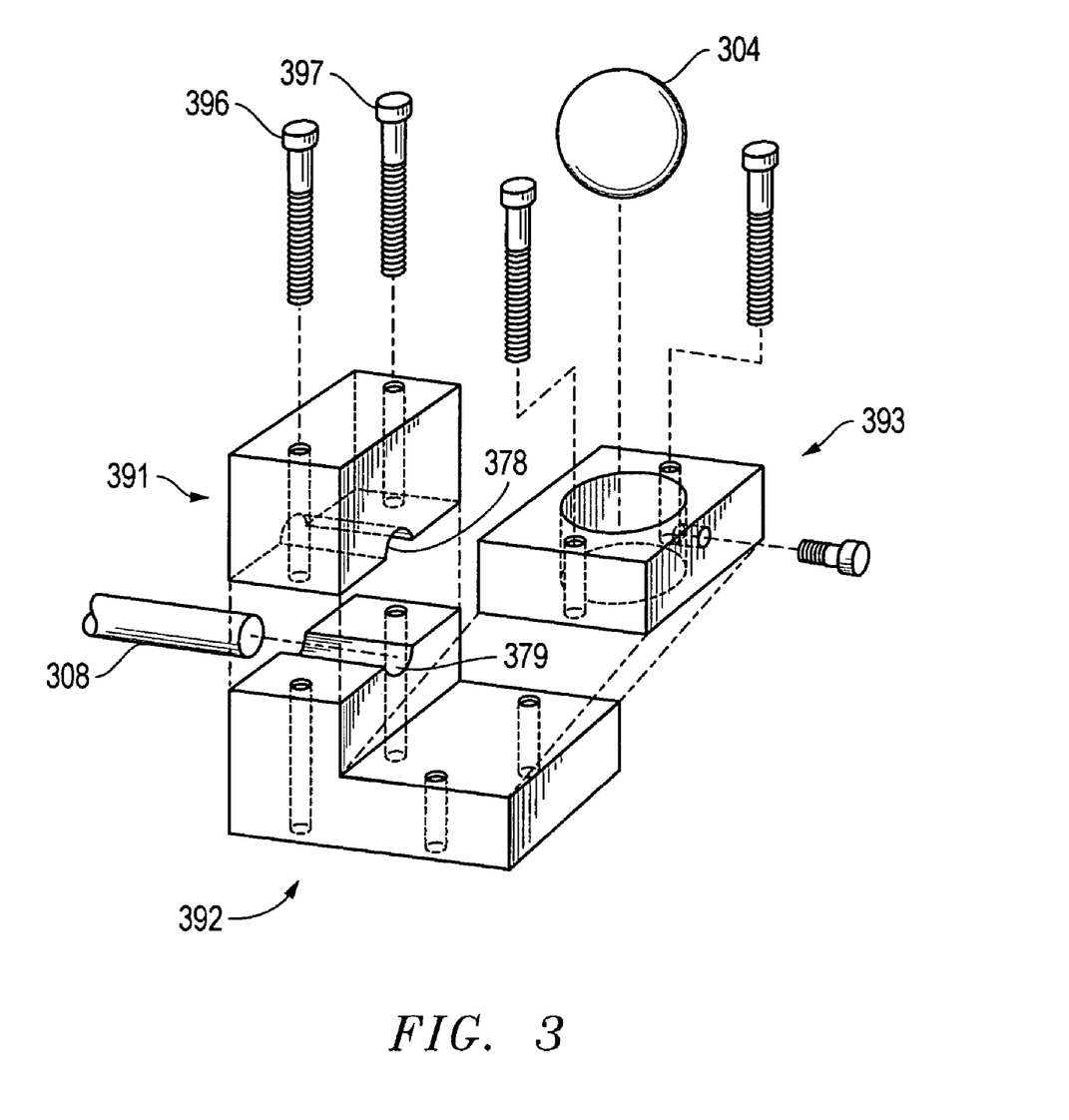
FIG. 3 is a prospective elevation of a spherical workpiece chuck and actuator rod end.

With reference to FIG. 3, grooves 378 and 379 are disposed on clamping plate 391 and support plate 392, and dimensioned such that when clamping plate 391 and support plate 392 are fastened together they form a socket within which actuator rod 308, which is equivalent to actuator rod 208 of FIG. 2 and its equivalents disclosed elsewhere in this document, can be placed. Grooves 379 and 378 are dimensioned such that they provide snug or press fit between the outer diameter of actuator rod 308 and the walls of grooves 378 and 379 when actuator rod 308 is placed into grooves 378 and 379.

The depth of grooves 378 and 379 is such that when actuator rod 308 is placed within either groove, up to one-half of the diameter of actuator rod 308 is contained within the groove. When fasteners 396 and 397 are employed to fasten clamping plate 391 to support plate 392 with actuator rod 308 disposed within grooves 378 and 379, support plate 392 is thereby rigidly fixed to actuator rod 308. Thus, the assembly of support plate 392 with clamping plate 391 and spherical workpiece chuck 393 provides a method of rigidly fastening spherical workpiece 304 to actuator rod 308.

With further reference to FIG. 2, actuator rod 208 passes through actuator rod support arm 210. Actuator rod support arm 210 acts as a support, guide, and bearing for actuator rod 208 as well as a method of sealing testing chamber 201 from the ambient environment.

With reference to FIG. 2, conduit 270, appended to actuator rod support arm 210 if it is desired to use a pressurized gas, serves to conduct fluid into annular space 231 between the inner diameter of actuator rod support arm 210 and the outer diameter of actuator rod 208. During a test using pressurized gas, annular space 231 is flushed with preferably nitrogen gas supplied to the space by conduit 270 appended to actuator rod support arm 210. The gas passing into annular space 231 passes along the annular space traveling away from testing chamber 201 toward the open end 233 of actuator rod support arm 210. In this manner annular space 231 purge gas reaches the ambient environment surrounding actuator rod support arm 210.

The outside diameter of actuator shaft 208 and the inside diameter of actuator rod support arm 210 are machined to close tolerance. To minimize binding and striction as actuator rod 208 passes along actuator rod support arm 210 the true of both the bore in actuator rod support arm 210 and the shaft comprising actuator rod 208 is also maintained to a low incidence of deviation. The combination of the small clearance between actuator rod 208 and the bore in actuator rod support arm 210 together with the low deviation from linearity of the actuator rod 208 and the bore through actuator rod support arm 210 (sometimes referred to collectively as "close tolerances") is effective alone, to maintain the lubricating media at a pressure gradient sufficient to simulate engine conditions between the testing chamber 201 and the outside of the testing chamber, while permitting the actuator rod 208 to move freely through the longitudinal retaining bore. A suitable pressure gradient is about 100 psi or more, preferably at least about 150 psi or more, more preferably at least about 160 psi or more, most preferably about 200 psi or more. In this manner, fluid under pressure residing in testing chamber 201 may be contained without the load of a mechanical seal impinging on actuator rod 208. The clearance between the inside diameter of the bore through actuator rod support arm 210 and the outside diameter of the shaft comprising actuator rod 208 is preferably about 0.0005 inches; with the true of the bore and shaft held to a deviation of less than 100 microns.

Many different construction materials and techniques for actuator rod 208 and actuator rod support arm 210 will be readily apparent to one skilled in the art and may be substituted with equal effectiveness. As stated previously, mechanical sealing devices are not preferred. Mechanical sealing devices are subject to chemical attack, mechanical degradation, and impart drag and load to the actuator rod which can effect the precision of the motion imparted to the workpieces contained in the testing chamber via the actuator rod.

Preferably, close tolerances alone, or in combination with a high-pressure gas, are used to seal actuator rod 208 through actuator support arm 210. An advantage in using a differential pressure gas flow to effect sealing and act as a bearing element is that fire hazard is reduced because of the diluting effect of the purge gas in the event of leakage along annular space 231. Another advantage includes that wear of the sealing element is eliminated, effecting simpler equipment setup and maintenance. Additionally, the incompatibility between the corrosive lubricating media and the seal or packing materials used to seal the testing chamber is eliminated.

The preferred manner of constructing actuator rod 208 and actuator rod support arm 210 is to use the plunger and barrel of a commercially available diesel fuel injector unit. Further features of the modifications are described in U.S. Pat. No. 6,546,782 B1. An example of a commercially available fuel injector unit having a suitable barrel and plunger is a commercial unit manufactured by Cummins Engine Company and contains all the fitments and conduits necessary to be used in the subject testing apparatus as received.

Figure 4:
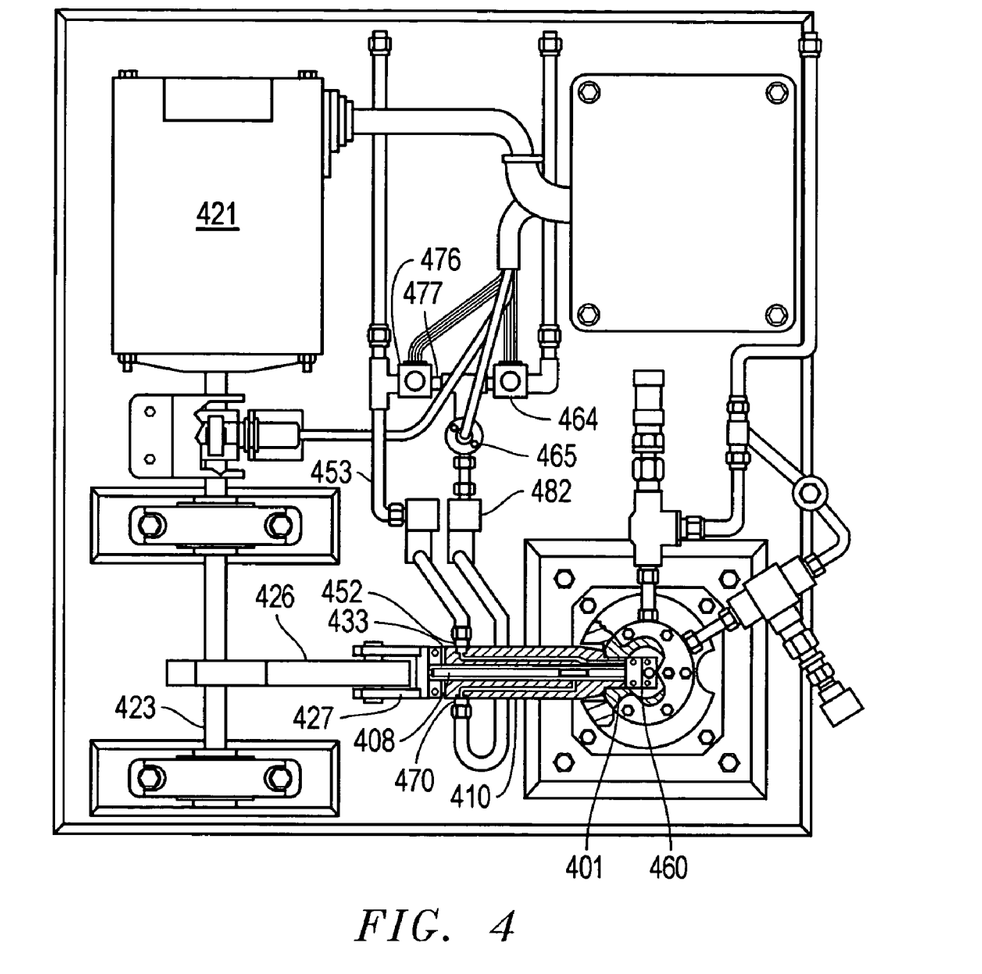
FIG. 4 is a plan view of the preferred embodiment of the testing apparatus.

Testing chamber 401 is the equivalent to testing chamber 101 of FIG. 1 and its equivalents disclosed elsewhere in this document. With further reference to FIG. 4, valve 482 is used to supply high-pressure gas to the annular space 433 between actuator rod 408 and the bore through actuator rod support arm 410. Actuator rod 408 and actuator rod support arm 410 are equivalent to, with reference to FIG. 2, actuator rod 208 and actuator rod support arm 210 respectively, and their respective equivalents disclosed elsewhere in this document.

With further reference to FIG. 4, workpiece holding and contacting assembly 460 is fastened to actuator rod 408. Testing chamber 401 is sealed at the point where actuator rod 408 passes through it by close tolerances either alone or in combination with high-pressure gas supplied to the annular space 433 via conduit 470 in the manner described above. The actuator rod 408 responds to motion derived from electric motor 421 via clamping assembly 427, crank arm 426, and drive shaft 423. The rotary motion of motor 421 is converted to reciprocating motion by a rotational axis adjuster (not shown) interposed between shaft 423 and crank arm 426.

With further reference to FIG. 4, valve 464, which is connected by a tee fitting to valves 477 and 465, permits an operator to use a common gas source to supply gas for pressurizing annular space 433 in actuator rod support arm 410 and to purge the corrosive lubricating media supply conduits 452 and 453.

Figure 5:
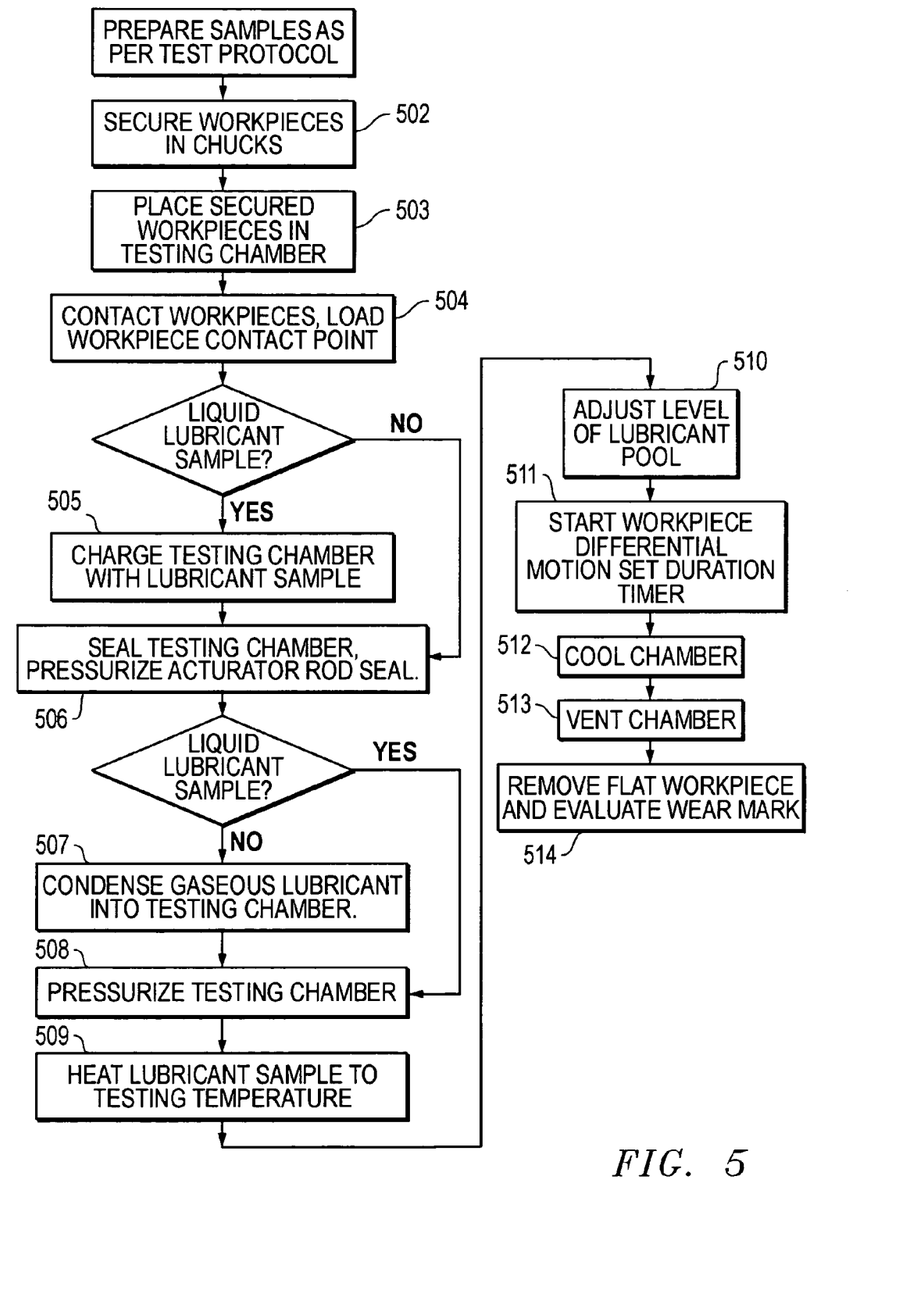
FIG. 5 is a block diagram of the testing methodology of the subject invention.

With further reference to FIG. 5, step 502 is to fasten the workpieces used to evaluate the lubricating properties of a lubricant medium into position in the testing apparatus. In accordance with ASTM testing protocol D6079, this calls for fastening a flat workpiece into a flat workpiece chuck and a spherical workpiece into a spherical workpiece chuck. Step 503 calls for placing the workpieces into the testing chamber. At this point any mechanical adjustments required are also made. The stroke length preferably is adjusted by a double nested eccentric type of rotational axis adjuster. The stroke length is also set at this time and temperature and test duration controls are also set. Preferably, in carrying out ASTM testing protocol D6079, spherical workpiece chuck bearing the spherical workpiece is fastened to the actuator rod end residing inside the testing chamber. The flat workpiece chuck bearing the flat workpiece is fastened to the workpiece loading device and enters the chamber when the workpiece loading device is placed into the testing chamber bore. In step 504, the workpieces are contacted and a load specified by the testing protocol being followed is applied to the contact area between the workpieces. In ASTM testing method D6079 this load is specified at 200 grams. Other testing protocols may require heavier or lighter loads. In some embodiments load is applied by a spring tension device, and in others the act of releasing the workpiece loading device once contact has been made between the workpieces loads the contact area by virtue of the weight of the combined workpiece loading device and associated workpiece chuck.

The next step depends upon whether the lubricant media being tested is a liquid or gas at standard atmospheric pressures and temperature (S.T.P.). If the corrosive lubricating media is a gas at S.T.P. conditions, step 505 is skipped. If the corrosive lubricating media is a liquid at S.T.P. conditions, step 505 is followed and a sample of the corrosive lubricating media is placed into the testing chamber until it covers the contact area between the two workpieces.

With further reference to FIG. 5, in step 506 the testing chamber is sealed by securing the testing chamber cap and by supplying gas pressure to the annular space between the actuator rod and the actuator rod support arm. Step 507 is next followed only if the composition to be tested for lubricating properties is an S.T.P. gas (if step 505 was bypassed). In this step the the corrosive lubricating media is introduced into the chamber, either as a liquid under pressure, or condensed from the gas phase by cooling a portion of the testing chamber with a source of the lubricating media attached to the testing chamber. Thus if step 507 is being followed, an amount of the corrosive lubricating media is introduced into the chamber at a pressure permitting it to remain a liquid until the contact area between the workpieces is covered by the liquid introduced into the testing chamber. In step 508, the testing chamber is pressurized with inert gas to a pressure that will simulate the conditions that the test protocol is designed to simulate when sufficient corrosive lubricating media has been charged into the testing chamber, step 509 is carried out. The testing chamber and the corrosive lubricating media are brought up to the testing temperature using the testing chamber heater and the heater controller is set to maintain the lubricant sample in the testing chamber at the temperature desired for the test. In a typical test this is less than about 200° C., but with the present application the temperature may be as much as about 500° C.

In step 510 the level of the corrosive lubricating media liquid contained in the testing chamber is adjusted to a level so that the contact area of the workpieces is just covered by the sample but not submerged in lubricating media. Adjustment of the liquid level is carried out using the eductor tube in the manner described above. In step 511, following adjustment of the lubricant level, differential motion is started between the workpieces, and the motion generator is adjusted to give a stroke rate called for in the testing protocol being followed. The ASTM testing protocol D6079 calls for a cycle rate of 50.0 cycles per second. The present application can be adjusted for rates of 0–60 cycles per second, which corresponds to drive motor revolutions of 0–3600 rpm. Once the proper cycle rate has been set, a timer is started that will shut off the driving motor at the end of the testing period. ASTM standard D6079 calls for a testing period of 75 minutes.

In step 512, once the testing period has expired and the timer has shut off the driving motor, the chamber is cooled to room temperature. Step 513 is then carried out in which residual pressure in the testing chamber is vented out of the testing chamber and along with it any lubricant material that is either in gas phase or has become entrained in the vent stream. After the testing chamber has been cooled to room temperature and all of the pressure has been vented from it, in step 514 the chamber is opened and flat workpiece is removed from it. Spherical workpiece is then evaluated according to the testing protocol being employed for wear. In ASTM testing protocol D6079 this involves measuring the major and minor axis of the elliptical scar worn into the spherical workpiece to asses how well the lubricant sample performed. Other testing protocols may employ different evaluation procedures.

With further reference to FIG. 2, the testing chamber 201 is sealed by securing the testing chamber cap and if it is desired to use pressurized gas, by supplying gas pressure to the annular space between the actuator rod and the actuator rod support arm. In this step the corrosive lubricating media is introduced into the chamber, either as a liquid under pressure, or condensed from the gas phase by cooling a portion of the testing chamber with a source of the corrosive lubricating media attached to the testing chamber. An amount of the corrosive lubricating media is introduced into the chamber at a pressure permitting it to remain a liquid until the contact area between the workpieces is covered by the liquid introduced into the testing chamber. When using DME, for example, the pressure within the testing chamber must be at least about 70 psi to maintain the DME in a liquid state. The testing chamber is pressurized with inert gas to a pressure that will simulate the conditions that the test protocol is designed to simulate. The testing chamber and corrosive lubricating media are brought up to the testing temperature using the testing chamber heater and the heater controller to maintain the lubricant sample in the testing chamber at the temperature desired for the test. In a typical test the temperature is from about 20° C. to about 500° C., preferably, about 200° C.

The corrosive lubricating media liquid contained in the testing chamber is adjusted to a level so that the contact area of the workpieces is just covered by the sample but not submerged in corrosive lubricating media. Adjustment of the liquid level is carried out using the eductor tube in the manner described above.

The application will be better understood with reference to the following example, which are illustrative only:

EXAMPLE 1

A pressure test was performed using the testing chamber of FIG. 1, including a diesel injector. The test was performed for one hour using diesel fuel, at a stroke length of 1 mm, and a sliding speed of 50 Hz. The opposite side of the diesel injector was not pressurized with gas. In other words, pressurized gas was not used to maintain a seal. The close tolerances, alone, maintained the pressure within the system at 164.0 psig or more for 1 hour.

| Time (minutes) | Pressure (psig) |
| --- | --- |
| 0 | 203.4 |
| 10 | 197.1 |
| 20 | 190.3 |
| 30 | 184.3 |
| 40 | 179.0 |
| 50 | 170.0 |
| 60 | 164.0 |

Persons of ordinary skill in the art will recognize that many modifications may be made to the present application without departing from the spirit and scope of the application. The embodiment described herein is meant to be illustrative only and should not be taken as limiting the application, which is defined in the claims.

We claim:

1. A method of safely testing at least one lubrication property of a flammable corrosive volatile lubricating media under operating engine conditions, said method comprising:
providing a testing chamber comprising a workpiece;
sealing said testing chamber using one or more features of an actuator rod selected from the group consisting of a deviation from linearity through a longitudinal retaining bore and a clearance through the longitudinal retaining bore, the one or more features being effective to maintain the lubricating media at a pressure gradient sufficient to simulate said engine conditions between the testing chamber and the outside of the testing chamber while permitting the actuator rod to move freely through the longitudinal retaining bore;
subjecting said workpiece to said operating engine conditions comprising a selected pressure and a selected temperature;
imparting to said workpiece a contact force having a magnitude and for a number of cycles effective to simulate said operating engine conditions; and,
providing a venting mechanism effective to prevent pressure in said testing chamber from exceeding maximum safe pressure.

2. The method of claim 1 wherein said method meets the requirements of ASTM testing specification D 6079.

3. The method of claim 1 wherein the lubricating media is selected from the group consisting of dimethyl ether (DME), methyl tertiary-butyl ether (MTBE), ethyl tertiary-butyl ether (ETBE), ethanol, and methanol.

4. The method of claim 2 wherein the lubricating media is selected from the group consisting of dimethyl ether (DME), methyl tertiary-butyl ether (MTBE), ethyl tertiary-butyl ether (ETBE), ethanol, and methanol.

5. The method of claim 1 wherein said pressure gradient is at least about 100 psi or more.

6. The method of claim 1 wherein said pressure gradient is at least about 150 psi or more.

7. The method of claim 1 wherein said pressure gradient is at least about 160 psi or more.

8. The method of claim 4 wherein said pressure gradient is at least about 100 psi or more.

9. The method of claim 4 wherein said pressure gradient is at least about 150 psi or more.

10. The method of claim 4 wherein said pressure gradient is at least about 160 psi or more.

11. The method of claim 1 wherein said pressurizing comprises feeding inert gas under pressure to said testing chamber.

12. The method of claim 11 wherein said inert gas is selected from the group consisting of nitrogen, helium, argon, and combinations thereof.

13. The method of claim 11 wherein said gas is nitrogen.

14. The method of claim 1 wherein said selected temperature is from about 20° C. to about 500° C.

15. The method of claim 2 wherein said selected temperature is from about 20° C. to about 500° C.

16. The method of claim 3 wherein said selected temperature is from about 20° C. to about 500° C.

17. The method of claim 4 wherein said selected temperature is from about 20° C. to about 500° C.

18. The method of claim 1 wherein said deviation from linearity is about 100 microns or less.

19. The method of claim 2 wherein said deviation from linearity is about 100 microns or less.

20. The method of claim 3 wherein said deviation from linearity is about 100 microns or less.

21. The method of claim 4 wherein said deviation from linearity is about 100 microns or less.

22. The method of claim 18 wherein the sealing of said testing chamber is accomplished by providing a clearance through the longitudinal retaining bore of about 0.0005 inches.

23. The method of claim 19 wherein the sealing of said testing chamber is accomplished by providing a clearance through the longitudinal retaining bore of about 0.0005 inches.

24. The method of claim 20 wherein the sealing of said testing chamber is accomplished by providing a clearance through the longitudinal retaining bore of about 0.0005 inches.

25. The method of claim 21 wherein the sealing of said testing chamber is accomplished by providing a clearance through the longitudinal retaining bore of about 0.0005 inches.

26. The method of claim 1 wherein said providing a venting mechanism comprises providing a mechanical pop-off valve and a blow-out panel effective to prevent said pressure in said testing chamber from exceeding maximum safe pressure.

27. The method of claim 2 wherein said providing a venting mechanism comprises providing a mechanical pop-off valve and a blow-out panel effective to prevent said pressure in said testing chamber from exceeding maximum safe pressure.

28. The method of claim 3 wherein said providing a venting mechanism comprises providing a mechanical pop-off valve and a blow-out panel effective to prevent said pressure in said testing chamber from exceeding maximum safe pressure.

29. The method of claim 22 wherein said providing a venting mechanism comprises providing a mechanical pop-off valve and a blow-out panel effective to prevent said pressure in said testing chamber from exceeding maximum safe pressure.

30. The method of claim 23 wherein said providing a venting mechanism comprises providing a mechanical pop-off valve and a blow-out panel effective to prevent said pressure in said testing chamber from exceeding maximum safe pressure.

31. The method of claim 24 wherein said providing a venting mechanism comprises providing a mechanical pop-off valve and a blow-out panel effective to prevent said pressure in said testing chamber from exceeding maximum safe pressure.

32. The method of claim 25 wherein said providing a venting mechanism comprises providing a mechanical pop-off valve and a blow-out panel effective to prevent said pressure in said testing chamber from exceeding maximum safe pressure.

33. The method of claim 1 wherein said maximum safe pressure is about 3400 psi.

34. The method of claim 2 wherein said maximum safe pressure is about 3400 psi.

35. The method of claim 3 wherein said maximum safe pressure is about 3400 psi.

36. The method of claim 4 wherein said maximum safe pressure is about 3400 psi.

37. The method of claim 29 wherein said maximum safe pressure is about 3400 psi.

38. The method of claim 30 wherein said maximum safe pressure is about 3400 psi.

39. The method of claim 31 wherein said maximum safe pressure is about 3400 psi.

40. The method of claim 32 wherein said maximum safe pressure is about 3400 psi.

41. A method of safely testing at least one lubrication property of DME under operating engine conditions, said method comprising:
providing a testing chamber comprising a workpiece;
sealing said testing chamber using one or more features of an actuator rod selected from the group consisting of a deviation from linearity through a longitudinal retaining bore and a clearance through the longitudinal retaining bore, the one or more features being effective to maintain the DME at a pressure of about 70 psi or more between the testing chamber and the outside of the testing chamber while permitting the actuator rod to move freely through the longitudinal retaining bore;
subjecting said workpiece to said operating engine conditions comprising a selected pressure and a selected temperature;
imparting to said workpiece a contact force having a magnitude and for a number of cycles effective to simulate said operating engine conditions; and,
providing a venting mechanism effective to prevent pressure in said testing chamber from exceeding maximum safe pressure.

42. The method of claim 41 wherein said method meets the requirements of ASTM testing specification D 6079.

43. The method of claim 41 wherein said pressure gradient is at least about 100 psi.

44. The method of claim 41 wherein said pressure gradient is at least about 150 psi.

45. The method of claim 41 wherein said pressure gradient is at least about 160 psi.

46. The method of claim 42 wherein said pressure gradient is at least about 100 psi.

47. The method of claim 42 wherein said pressure gradient is at least about 150 psi.

48. The method of claim 42 wherein said pressure gradient is at least about 160 psi.

49. The method of claim 41 wherein said pressurizing comprises feeding inert gas under pressure to said testing chamber.

50. The method of claim 49 wherein said inert gas is selected from the group consisting of nitrogen, helium, argon, and combinations therof.

51. The method of claim 49 wherein said gas is nitrogen.

52. The method of claim 41 wherein said selected temperature is from about 20° C. to about 500° C.

53. The method of claim 42 wherein said selected temperature is from about 20° C. to about 500° C.

54. The method of claim 41 wherein said deviation from linearity is about 100 microns or less.

55. The method of claim 42 wherein said deviation from linearity is about 100 microns or less.

56. The method of claim 41 wherein the sealing of said testing chamber is accomplished by providing a clearance through the longitudinal retaining bore of about 0.0005 inches.

57. The method of claim 42 wherein the sealing of said testing chamber is accomplished by providing a clearance through the longitudinal retaining bore of about 0.0005 inches.

58. The method of claim 41 wherein said providing a venting mechanism comprises providing a mechanical pop-off valve and a blow-out panel effective to prevent said pressure in said testing chamber from exceeding maximum safe pressure.

59. The method of claim 42 wherein said providing a venting mechanism comprises providing a mechanical pop-off valve and a blow-out panel effective to prevent said pressure in said testing chamber from exceeding maximum safe pressure.

60. The method of claim 41 wherein said maximum safe pressure is about 3400 psi.

61. The method of claim 42 wherein said maximum safe pressure is about 3400 psi.

62. The method of claim 55 wherein said maximum safe pressure is about 3400 psi.

63. The method of claim 56 wherein said maximum safe pressure is about 3400 psi.

64. A method of safely testing at least one lubrication property of DME under operating engine conditions, said method comprising:
providing a testing chamber comprising a workpiece;
sealing said testing chamber using one or more features of an actuator rod selected from the group consisting of a deviation from linearity through a longitudinal retaining bore and a clearance through the longitudinal retaining bore, the one or more features being effective to maintain the DME at a pressure gradient of about 100 psi or more between the testing chamber and the outside of the testing chamber while permitting the actuator rod to move freely through the longitudinal retaining bore;

subjecting said workpiece to said operating engine conditions comprising a pressure of at least about 70 psi and a selected temperature;

imparting to said workpiece a contact force having a magnitude and for a number of cycles effective to simulate said operating engine conditions;

providing a venting mechanism effective to prevent pressure in said testing chamber from exceeding maximum safe pressure.

65. The method of claim 64 wherein said method meets the requirements of ASTM testing specification D 6079.

66. The method of claim 64 wherein said pressurizing comprises feeding inert gas under pressure to said testing chamber.

67. The method of claim 66 wherein said inert gas is selected from the group consisting of nitrogen, helium, argon, and combinations therof.

68. The method of claim 66 wherein said gas is nitrogen.

69. The method of claim 65 wherein said pressurizing comprises feeding inert gas under pressure to said testing chamber.

70. The method of claim 69 wherein said inert gas is selected from the group consisting of nitrogen, helium, argon, and combinations therof.

71. The method of claim 69 wherein said gas is nitrogen.

72. The method of claim 69 wherein said selected temperature is from about 20° C. to about 500° C.

73. The method of claim 69 wherein said selected temperature is from about 20° C. to about 500° C.

74. The method of claim 71 wherein said selected temperature is from about 20° C. to about 500° C.

75. The method of claim 64 wherein said deviation from linearity is about 100 microns or less.

76. The method of claim 72 wherein said deviation from linearity is about 100 microns or less.

77. The method of claim 74 wherein said deviation from linearity is about 100 microns or less.

78. The method of claim 75 wherein the sealing of said testing chamber is accomplished by providing a clearance through the longitudinal retaining bore of about 0.0005 inches.

79. The method of claim 76 wherein the sealing of said testing chamber is accomplished by providing a clearance through the longitudinal retaining bore of about 0.0005 inches.

80. The method of claim 77 wherein the sealing of said testing chamber is accomplished by providing a clearance through the longitudinal retaining bore of about 0.0005 inches.

81. The method of claim 78 wherein said providing a venting mechanism comprises providing a mechanical pop-off valve and a blow-out panel effective to prevent said pressure in said testing chamber from exceeding maximum safe pressure.

82. The method of claim 79 wherein said providing a venting mechanism comprises providing a mechanical pop-off valve and a blow-out panel effective to prevent said pressure in said testing chamber from exceeding maximum safe pressure.

83. The method of claim 80 wherein said providing a venting mechanism comprises providing a mechanical pop-off valve and a blow-out panel effective to prevent said pressure in said testing chamber from exceeding maximum safe pressure.

84. The method of claim 81 wherein said maximum safe pressure is about 3400 psi.

85. The method of claim 82 wherein said maximum safe pressure is about 3400 psi.

86. The method of claim 83 wherein said maximum safe pressure is about 3400 psi.

* * * * *